(12) United States Patent
Lee et al.

(10) Patent No.: US 11,484,616 B2
(45) Date of Patent: Nov. 1, 2022

(54) SOLID FRAGRANCE COMPOSITION AND METHOD FOR MANUFACTURING SAME

(71) Applicant: MASSCON CO., LTD., Seoul (KR)

(72) Inventors: Yongeui Lee, Gyeonggi-do (KR); Min Young Cheong, Gyeonggi-do (KR); Chang Bin Lee, Busan (KR)

(73) Assignee: MASSCON CO., LTD., Seoul (KR)

( * ) Notice: Subject to any disclaimer, the term of this patent is extended or adjusted under 35 U.S.C. 154(b) by 0 days.

(21) Appl. No.: 17/252,633

(22) PCT Filed: Jun. 12, 2019

(86) PCT No.: PCT/KR2019/007037
§ 371 (c)(1),
(2) Date: Dec. 15, 2020

(87) PCT Pub. No.: WO2020/004832
PCT Pub. Date: Jan. 2, 2020

(65) Prior Publication Data
US 2021/0260237 A1 Aug. 26, 2021

(30) Foreign Application Priority Data
Jun. 27, 2018 (KR) ........................ 10-2018-0073895

(51) Int. Cl.
*A61L 9/012* (2006.01)
*A61M 21/00* (2006.01)

(52) U.S. Cl.
CPC ............ *A61L 9/012* (2013.01); *A61M 21/00* (2013.01); *A61L 2209/13* (2013.01); *A61M 2021/0016* (2013.01)

(58) Field of Classification Search
CPC ...................................................... A61L 9/012
See application file for complete search history.

(56) References Cited

FOREIGN PATENT DOCUMENTS

| CN | 103349789 A | 10/2013 |
|---|---|---|
| JP | 6-47086 A | 2/1994 |
| JP | 7-75666 A | 3/1995 |
| KR | 10-1993-008909 B1 | 9/1993 |
| KR | 10-1999-0058712 A | 7/1999 |

(Continued)

OTHER PUBLICATIONS

English Machine Translation for KR2003-0043303 A Obtained Sep. 28, 2021 at: http://translationportal.epo.org/emtp/translate/?ACTION=claims-retrieval&COUNTRY=KR (Year: 2004).*

(Continued)

*Primary Examiner* — Arrie L Reuther
(74) *Attorney, Agent, or Firm* — Christensen, Fonder, Dardi & Herbert PLLC; Diane E. Bennett; Peter S. Dardi

(57) ABSTRACT

The present invention relates to a solid fragrance composition which can improve the load rate of a fragrant material, can selectively load a fragrance which can be acquired during the aging process of a mixed fragrant material, maintain the fragrance from the beginning of the loading, and improve the longevity of the fragrance at a uniform strength. In addition, the issue of being harmful to the human body can be resolved by reducing powder flying around, and stability at a high temperature can be improved so as to be applied in various environments.

6 Claims, 4 Drawing Sheets

(56) References Cited

FOREIGN PATENT DOCUMENTS

| KR | 10-0422306 B1 | 3/2004 |
| KR | 10-2003-0043303 A | 11/2004 |
| KR | 10-0972505 B1 | 7/2010 |
| KR | 10-2011-0129505 A | 12/2011 |
| KR | 10-1375125 B1 | 3/2014 |
| KR | 20-2018-0001809 U | 4/2019 |

OTHER PUBLICATIONS

Office Action from corresponding Korean Patent Application No. 10-2018-0073895 dated Feb. 4, 2020 (Google translation).
International Search Report for Patent Application No. PCT/KR2019/007037 dated Sep. 11, 2019.
Office Action from corresponding Chinese Patent Application No. 201980043820.X dated Nov. 18, 2021. (google trans).

* cited by examiner

Before loading fragrant materialAfter loading fragrant material

Before loading fragrant material      After loading fragrant material

SOLID FRAGRANCE COMPOSITION AND METHOD FOR MANUFACTURING SAME

CROSS REFERENCE TO RELATED APPLICATIONS

This application is a National Stage filing of PCT Application No. PCT/KR2019/007037 filed Jun. 12, 2019, entitled "Solid Fragrance Composition and Method for Manufacturing Same", which claims priority to Korean Patent Application No. KR 10-2018-0073895 filed Jun. 27, 2018, both of which are incorporated herein by reference.

BACKGROUND OF THE INVENTION

1. Field of the Invention

The present invention relates to a solid fragrance composition having a high load rate of a fragrant material.

In addition, the present invention relates to a solid fragrance composition which can delay or stop aging in order to achieve a desired fragrance at a specific stage during combining fragrant materials and can improve retention of fragrance and persistence of fragrance while suppressing deterioration of loaded fragrance.

In addition, the present invention relates to a solid fragrance composition suppressing a powder flying phenomenon.

In addition, the present invention relates to a method for manufacturing the solid fragrance composition as described above.

2. Description of the Related Art

Fragrances can change emotions of animals including humans, and are also used in aromatherapy to improve mental and physical health with a feeling of relief, pleasure, tension, arousal, meditation, etc. Fragrances can be provided in the form of perfumes, scented candles, diffusers, etc. In order to meet the needs of consumers, there is a growing trend of specialized stores for commercializing, such as forming perfume containers or scented candles in the shape of animals, foods, film characters, etc., for example.

In general, the fragrance composition emits fragrance into the atmosphere by using a diffuser to replenish a bottle with a fragrant substance such as oil, spraying or dropping a fragrant substance on gypsum, etc., or dropping or mixing a small amount of fragrant substance on a solid support such as scented candles.

However, the replenishing the bottle with oil may result in loss of oil and damage to the bottle. The use of gypsum may result in a problem of powder flying. In the case of scented candles, there is a risk of fire due to the necessity of ignition. In addition, since the fragrance components have different degrees of volatilization, there are common problems in that the initial fragrance can be easily deteriorated without a long lasting, due to preferential volatilization of the fragrance components having high volatility. In addition, in the spraying or dropping a fragrant substance on gypsum, etc., the use time is very short as the fragrance disappears quickly due to a low content of the fragrant material, and there is an inconvenience of repeatedly spraying or dropping.

In general, in order to achieve the desired fragrance by using a liquid fragrant material (perfuming), the steps of (1) mixing selected various fragrant materials in a desired ratio, (2) aging the mixed fragrant materials, and (3) testing the fragrance after aging are performed. If the desired fragrance is not achieved in the test after aging, the step (3) should be repeated until the desired fragrance is achieved. Here, aging refers to a process in which the fragrance of the mixed fragrant materials continuously changes and is a natural phenomenon that cannot be stopped artificially. The aging period is variable for each fragrant material, but may be about 1 to 3 months on average. In other words, it takes a lot of time to achieve a desired fragrance.

Moreover, even if you want to realize the fragrance at a specific point during aging, there is a fatal problem that it is not possible to realize the desired fragrance as a product because aging is an unstoppable natural phenomenon.

In addition, in the case of conventional gel fragrances and solid fragrances, there are problems that the initial strength of fragrance is weak and the use time is extremely short due to the low load rate of fragrance. Accordingly, in order to improve emission rate of fragrance, controllability of emission rate and persistence of fragrance and to facilitate the emission of fragrance in various environments, attempts have been made to microencapsulate a liquid fragrant material by coating with a polymer or to load fragrance in a porous substance. However, it does not reach the completion of development in the commercialization stage.

Therefore, development of technology is absolutely required for fragrance-related products, such as (1) delaying or stopping aging in order to achieve a desired fragrance at a specific stage during combining fragrant materials, (2) suppressing deterioration of fragrance and improving ease of use of liquid fragrant material and (3) improving the amount of emission of fragrance and the duration of emission time of solid fragrances.

SUMMARY OF THE INVENTION

The present invention is aimed to provide a fragrance composition having a high load rate of fragrant material, for delaying or stopping aging in order to achieve a desired fragrance at a specific stage during combining fragrant materials, and for improving retention of loaded fragrance and persistence of fragrance.

In addition, the present invention relates to a solid fragrance composition suppressing a powder flying phenomenon.

In addition, the present invention relates to a method for manufacturing the fragrance composition as described above.

In order to solve the above problems, the present invention provides a solid fragrance composition, comprising porous particles having a plurality of pores, a gel matrix for binding the porous particles to each other, and a fragrant material contained in the pores of the porous particle, wherein a weight ratio of the gel matrix and the porous particles is 1:3 to 30.

According to one embodiment, the porous particles may be at least one selected from the group consisting of silica, zeolite, activated carbon and acrylic resin particles.

According to one embodiment, the gel matrix may be at least one selected from the group consisting of agar, carrageenan, gellan gum and gelatin.

According to one embodiment, an average particle size of the porous particles may be 1 to 100 μm.

According to one embodiment, an average pore diameter of the porous particles may be 1 to 100 nm.

According to one embodiment, a load rate of the fragrant material according to Equation 1 may be 100 to 500%.

Load rate (%)=(maximum weight of loaded fragrant material (g)/weight of support (g))×100, where weight of support=total weight of the porous
particles and the gel matrix. [Equation 1]

According to one embodiment, the gel matrix may have voids, wherein an average void diameter may be 0.1 to 100 μm and the voids have the fragrant material contained therein.

Another aspect of the present invention, there is provided a method for manufacturing a solid fragrance composition, comprising:

1) dispersing porous particles in water;
2) adding a gel matrix to the dispersion of 1) and homogeneously mixing at high temperature;
3) injecting the mixture of 2) into a mold and cooling it to prepare a molded product; and
4) loading a fragrant material into the molded product of 3), wherein a weight ratio of the gel matrix and the porous particles is 1:3 to 30.

Other specifics of the embodiments of the present invention are included in the detailed description below.

Effect of the Invention

According to the solid fragrance composition and the method for manufacturing same of the present invention, it is possible to improve the load rate of a fragrant material, selectively load a fragrance which can be acquired during the aging process of a mixed fragrant material, maintain the fragrance from the beginning of the loading, and improve the longevity of the fragrance at a uniform strength. In addition, the issue of being harmful to the human body can be resolved by reducing powder flying around, and stability at a high temperature can be improved so as to be applied in various environments.

DETAILED DESCRIPTION OF THE INVENTION

Figure 1:
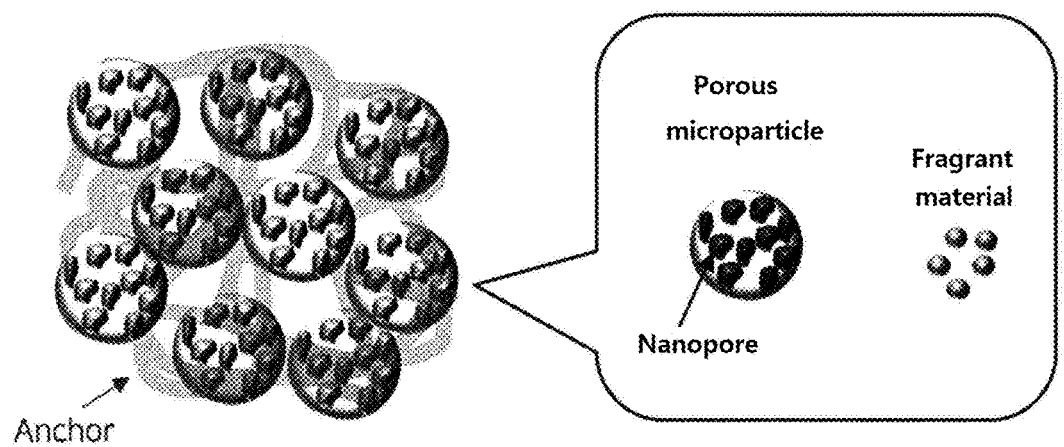
FIG. 1 schematically shows a structure of the composition.

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention. In the following description of the present invention, detailed description of known functions will be omitted if it is determined that it may obscure the gist of the present invention.

Since scent can affect moods and emotions of animals, it is applied in a variety of fields from daily life products to medical treatments. The type of fragrance can be classified according to volatile components and composition ratio of the fragrant material. In addition, since the composition ratio of the volatile component is variable when released for a long period, it tends to give off a different scent from the beginning. In particular, in the case of a natural fragrant materials, various kinds of fragrances are mixed for use, but there is a phenomenon (aging) in which the fragrance is denatured due to the change in the composition ratio of the fragrant material over time after combining fragrant materials. In order to load the natural scent during the aging process without change in scent, to maintain the fragrance from the beginning of the loading and to improve the longevity of the fragrance at a uniform strength, there is a need for a composition capable of increasing the load rate of fragrant material and emitting fragrance with a uniform strength.

The present invention is to provide a composition for solving such a problem. In addition, it is intended to provide a solid fragrance composition for improving stability and allowing for free forming of a shape during product processing by supplementing disadvantage such as powder flying.

Hereinafter, the solid fragrance composition and the method of manufacturing the same according to embodiments of the present invention will be described in more detail.

As used herein, the term "matrix" may be described interchangeably with "anchor" or "binder", and refers to a material having a fibrous structure, which exists in an inter-particle space and by which voids can be formed.

As used herein, the term "fragrant material" may be used interchangeably with "fragrance substance" and may include, for example, oil, hydrophilic solution, or a combination thereof.

Unless otherwise specified in the disclosure, the expression "to" as used with numerical values means an expression including the corresponding numerical value. Specifically, for example, the expression "1 to 2" means not only including 1 and 2, but also including all numerical values between 1 and 2.

The present invention provides a solid fragrance composition, comprising porous particles having a plurality of pores, a gel matrix for binding the porous particles to each other, and a fragrant material contained in the pores of the porous particles.

When using only porous particles or microparticles to load the fragrant material, disadvantages such as harm to the human body may occur due to powder flying after complete emitting of fragrance, so that the gel matrix is used to improve high temperature stability and to allow for free forming of a shape.

The weight ratio of the porous particles and the gel matrix may affect the load rate and molding stability. Specifically, when the weight ratio of the gel matrix is excessively increased, the content ratio of the porous particles, which is the main material on which the fragrant material is loaded, decreases, so that the load rate may decrease. On the other hand, when the weight ratio of the gel matrix is excessively decreased, it is difficult to stably bind the porous microparticles to each other, and thus a powder flying phenomenon may occur. Therefore, according to one embodiment, the weight ratio of the gel matrix and the porous particles may be 1:3 to 30, for example 1:4 to 20, for example 1:3 to 19.

According to one embodiment, the porous particles may include at least one selected from the group consisting of silica, zeolite, activated carbon, and acrylic resin particles.

For example, the acrylic resin particles may include poly (methylmethacrylate)(PMMA).

The porous particles are preferably materials harmless to the human body and environments and may further comprise an additional support. The porous particles have a very large surface area due to the formation of pores and form a three-dimensional skeletal structure, so that the fragrant material can be stably loaded without deterioration of fragrance. In addition, the porous particles, which are main components for loading the fragrant material, may serve to prevent deterioration of fragrance by gradually releasing the loaded fragrant material. As such, an average diameter of nanopores of the particles for effective loading, emission, and prevention of deterioration of fragrance may be, for example, 1 to 100 nm, for example, 10 to 100 nm, for example, 20 to 50 nm, and the average particle size (diameter) is 1 to 100 μm, for example, it may be 10 to 100 μm. In addition, in order to improve the load rate, the porosity of the porous particles may be, for example, 70% or more, for example, 80% or more, for example, 90% or more. A load rate of the fragrant material may be calculated according to Equation 1, and may have, for example, 100 to 500%, for example, 200 to 500%.

Load rate (%)=(maximum weight of loaded fragrant material (g)/weight of support (g))×100, where weight of support=total weight of the porous particles and the gel matrix. [Equation 1]

According to one embodiment, the gel matrix may comprise at least one selected from the group consisting of agar, carrageenan, gellan gum and gelatin. The gel matrix may have, for example, a fibrous structure and it serves to stably bind porous particles to each other and has a lot of voids formed between structures entangled with particles. The average void diameter of the gel matrix may be, for example, 0.1 to 100 μm, for example, 0.5 to 50 μm, for example, 1 to 20 μm. With such a void size, the micro-sized voids can serve as a channel for fixing porous particles and for loading and releasing the fragrant material. Moreover, the incorporation of the gel matrix causes no powder flying phenomenon after complete emitting of the fragrant material, so that products can be safely used and the composition can be formed in various shape.

According to one embodiment, the fragrant material may include, for example, aroma essential oil or essential oil, and may include, for example, an extract extracted with a water-soluble solvent. Specific examples of essential oils include lavender, grapefruit, geranium, cinnamon leaves, tea tree, cedarwood, orange, eucalyptus, bergamot, lemon, lime, mandarin, myrrh, neroli, niaouli, peppermint, pine, rosemary, chamomile, ylang-ylang, neem, frankincense, benzoin, helichrysum, phytoncide, rosewood, sandalwood, and the like. In addition, the fragrant material may be diluted with a carrier oil or a solvent. The carrier oil is, for example, one or more selected from the group consisting of grapeseed, evening primrose, rosehip, macadamia nuts, borage, safflower, sesame, St. John's wort oil, sweet almond, avocado, apricot kernel, olive, wheatgerm, calendula, carrot, coconut, hazelnut, jojoba, basil and almond. In addition, the fragrant material may further comprise a solvent and an additive, the solvent may include ethanol, water, glycerin, silicone oil and the like, and the additive may include pigments. In the present invention, the fragrant material is not limited to the main fragrance substances as described above and any conventional vegetable oil may be used without limitation. Other solvents and additives generally used for combining fragrant materials are included without particular limitation.

According to one embodiment, a method for manufacturing a fragrance composition may comprise:
1) dispersing porous particles in water;
2) adding a gel matrix to the dispersion of 1) and homogeneously mixing at high temperature;
3) injecting the mixture of 2) into a mold and cooling it to prepare a molded product; and
4) loading a fragrant material into the molded product of 3).

The solid fragrance composition of the present invention according to the above method may have a structure in which porous particles are distributed in a gel matrix structure, as shown in FIG. 1. In addition, by loading the fragrance in the pores of the porous particles and the voids of the gel matrix structure, it is possible to provide a sustained-release fragrance, improve persistence of fragrance, and prevent deterioration of the initial scent.

Hereinafter, embodiments of the present invention will be described in detail so that those skilled in the art can easily carry out the present invention. The present invention may, however, be embodied in many different forms and should not be construed as limited to the embodiments set forth herein.

Examples 1 to 6

A solid fragrance composition was prepared according to the composition shown in Table 1.

TABLE 1

| Ex. | Fragrant material | Porous particle | Gel matrix | Gel matrix:porous particle weight ratio |
|---|---|---|---|---|
| Example 1 | Lavender essential oil | Silica 9.5 g (Average pore diameter: 30~40 nm) | Agar 0.5 g | 1:19 |
| Example 2 | Lavender essential oil | Silica 9 g (Average pore diameter: 30~40 nm) | Agar 1 g | 1:9 |
| Example 3 | Lavender essential oil | Silica 8 g (Average pore diameter: 30~40 nm) | Agar 2 g | 1:4 |
| Example 4 | Lavender essential oil | Silica 9 g (Average pore diameter: 30~40 nm) | Carrageenan 1 g | 1:9 |
| Example 5 | Lavender essential oil | Silica 9 g (Average pore diameter: 30~40 nm) | Gellan gum 1 g | 1:9 |

TABLE 1-continued

| Ex. | Fragrant material | Porous particle | Gel matrix | Gel matrix:porous particle weight ratio |
|---|---|---|---|---|
| Example 6 | Lavender essential oil | Silica 9.7 g (Average pore diameter: 30~40 nm) | Agar 3 g | 1:3.2 |

As the porous particle, porous silica (average particle size: 5 to 15 μm) was used.

Porous particles were placed in a 70 ml vial, and agar and 50 g of purified water were added, followed by stirring. After raising the temperature of the vial to 100° C. and stirring for 30 minutes, it was poured into a mold of a certain shape and left at room temperature for at least 1 hour. When the molded product solidified, it was removed from the mold and dried in an oven at 70° C. for 5 hours or more, in this example for 10 hours, to remove moisture to prepare a molded support.

Figure 2:
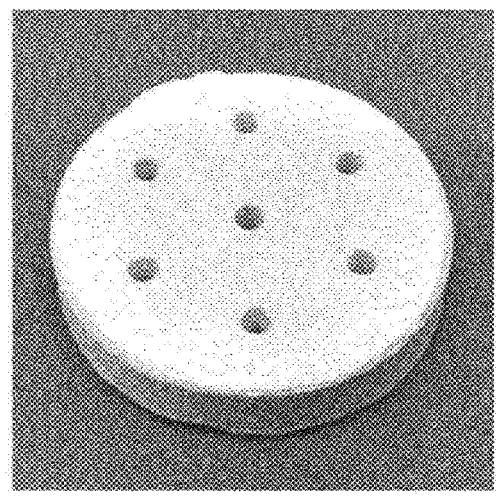
FIG. 2 and FIG. 5 are photographs showing the appearance of the solid compositions prepared in Examples and Comparative Examples before and after loading the fragrant material.
Figure 2:
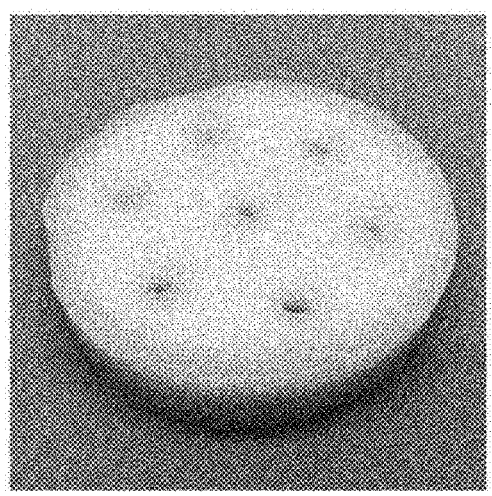

The support was put into a container containing lavender essential oil and left for 10 hours or more, in this example for 24 hours, to sufficiently load the fragrant material. FIG. 2 shows a photograph of the composition before and after loading the fragrant material on the composition of Example 1, and Examples 2 to 6 showed a similar appearance to that of Example 1, before and after loading of the fragrant material.

Figure 3:
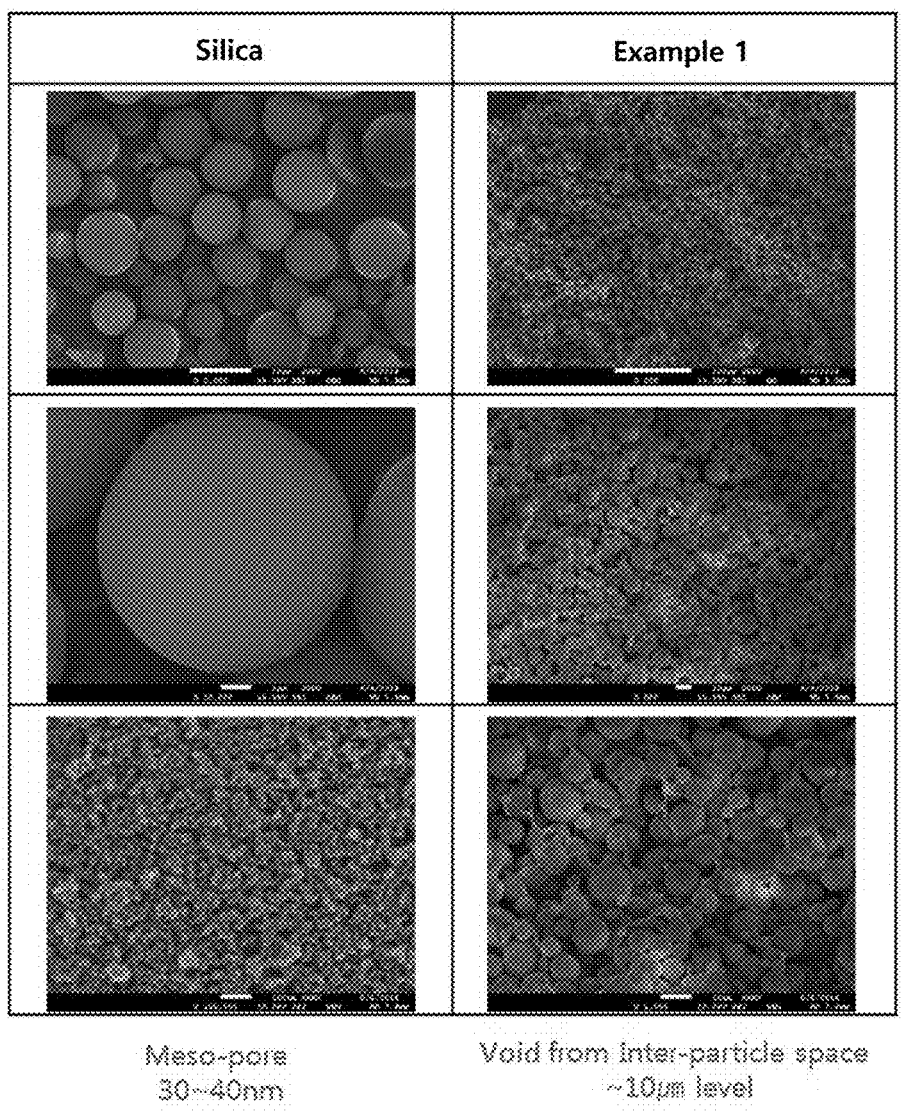
FIG. 3 is scanning electron microscope (SEM) photographs of silica and the composition according to Example 1.

In addition, FIG. 3 shows scanning electron microscope (SEM) photographs of silica used in the Example and the composition according to Example 1. As shown in FIG. 3, it is found that the pores of the silica have a diameter of 30 to 40 nm, and the voids between the silica particles have a diameter of about 10 μm.

Figure 4:
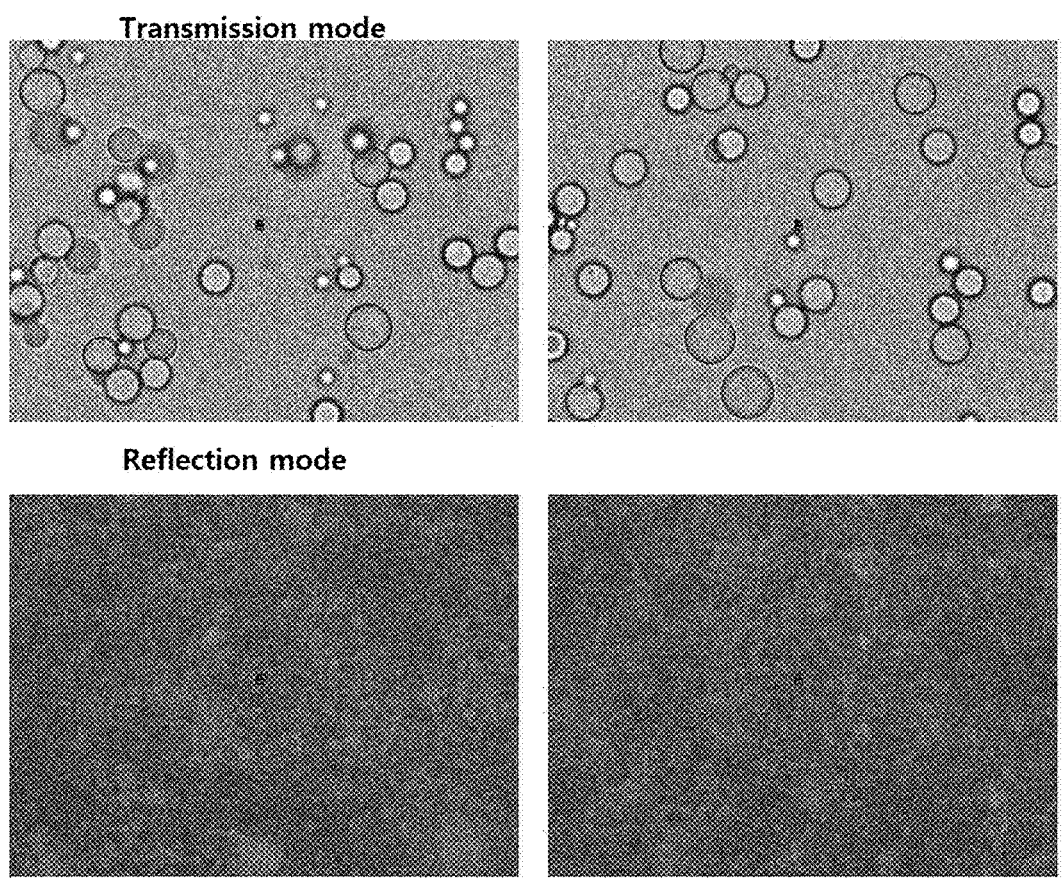
FIG. 4 is microscope photographs under transmission mode and reflection mode of the composition according to Example 1.

In addition, transmission mode and reflection mode observation photos with a microscope (BX53M/Olympus) for Example 1 are shown in FIG. 4, respectively. In the transmission mode of FIG. 4, the black line on the edge represents the outline of the particle, of which inside is a pore, and in the reflection mode, the white line on the edge represents the outline of the particle, of which black inside is a pore.

Comparative Examples 1 to 5

A fragrance composition was prepared according to the composition shown in Table 2.

TABLE 2

| Ex. | Fragrant material | Porous Particle | Gel matrix | Gel matrix:Porous particle weight ratio |
|---|---|---|---|---|
| Comparative Example 1 | Lavender essential oil | Silica 10 g (Average pore diameter < 10 nm) | — | — |
| Comparative Example 2 | Lavender essential oil | Silica 10 g (Average pore diameter < 30 nm) | — | — |
| Comparative Example 3 | Lavender essential oil | Silica 7 g (Average pore diameter < 30 nm) | Agar 3 g | 1:2.3 |
| Comparative Example 4 | Lavender essential oil | — | — | — |
| Comparative Example 5 | Lavender essential oil | — | Ethylene vinyl acetate (EVA) | — |

Comparative Examples 1 and 2

Figure 5:
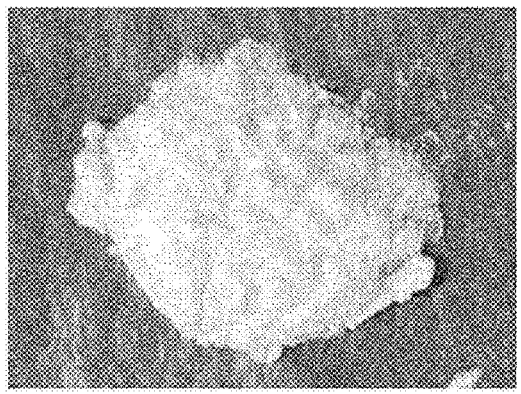
Figure 5:
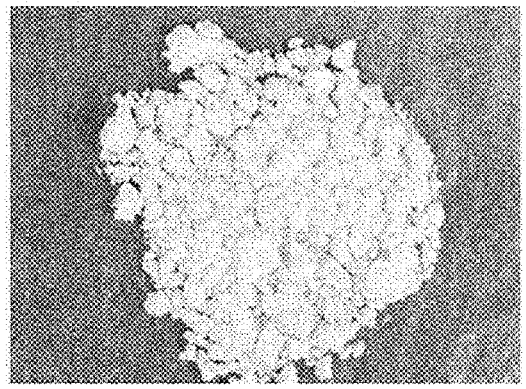

As the porous particle, porous silica (average particle size: 5 to 15 μm) was used. Porous particles were put in a 70 ml vial, lavender essential oil was added to the vial and a mixing ball was put in the vial, followed by mixing at 100 rpm in a rolling machine for 4 hours. Thereafter, the sample was collected. It was determined that the fragrant material was well loaded when there were almost no particles agglomerated on the inner wall of the vial. The maximum oil absorption relative to the support for maintaining a good loading state was defined as a load rate. FIG. 5 shows a visual observation image of the composition of Comparative Example 2 before and after loading the fragrant material.

Comparative Example 3

A fragrance composition was prepared in the same manner as in Example 1, except for the composition shown in Table 2.

Comparative Example 4

Lavender essential oil was used as it was.

Comparative Example 5

2 g of lavender essential oil was added to a sealed high-pressure vial. 8 g of ethylene vinyl acetate (EVA) (Dupont, Elvax) pellets were added to the vial, and stirred at a speed of 150 rpm for 2 hours while maintaining a temperature of 40° C. and a pressure of 40 cmHg. The above process was repeated by changing the amount of lavender essential oil. The maximum amount when lavender essential oil was completely loaded into the EVA pellets was defined as a load rate.

Experimental Example 1: Measurement of Load Rate of Fragrant Material

In order to measure the load rate of the fragrant material, the amount of the loaded fragrant material was measured relative to the weight of the support for each composition of Examples and Comparative Examples.

The load rate was calculated according to Equation 1, and the results are shown in Table 3.

Load rate (%)=(maximum weight of loaded fragrant material (g)/weight of support (g))×100, where weight of support=total weight of the porous particles and the gel matrix. [Equation 1]

TABLE 3

| Ex. | Load rate of fragrant material (%) |
|---|---|
| Comparative Example 1 | 30 |
| Comparative Example 2 | 200 |
| Comparative Example 3 | 100 |
| Comparative Example 4 | — |
| Comparative Example 5 | 20 |
| Example 1 | 260 |
| Example 2 | 250 |
| Example 3 | 200 |
| Example 4 | 230 |
| Example 5 | 240 |
| Example 6 | 210 |

As shown in Table 3, it can be seen that all the compositions according to Examples have a load rate of 200% or more. In particular, it is found that the load rate in all Examples increases by at least 10 times compared to Comparative Example 5, which is a conventional solid fragrance composition.

Experimental Example 2: Evaluation of Retention of Initial Scent and Persistence of Fragrance Sensory evaluation was performed according to the criteria shown in Table 4 to confirm the degree of deterioration of the initial scent according to each composition. A sample amount of each composition was taken based on 0.5 g of a fragrant material to have same amount of the fragrant material, and then it was placed in a glass petri dish. After the sample was stored for 15 days at room temperature, an evaluation test for retention of the initial scent was carried out by a panel trained in scent.

TABLE 4

| | Retention of initial scent |
|---|---|
| Grade | |
| 0 | Completely different kind of smell from the initial |
| 1 | Grading the degree of smell difference from to the |
| 2 | initial (The higher the number, the same smell as |
| 3 | the initial) |
| 4 | |
| 5 | Same smell as the initial |

In addition, sensory evaluation was performed according to the criteria shown in Table 5 to evaluate persistence of fragrance. A sample amount of each composition was taken based on 0.5 g of a fragrant material to have same amount of the fragrant material, and then it was placed in a 70 ml vial. The sample was put in a 1 L beaker while it was contained in a vial, and appropriate amount of purified water was filled therein. Then, the temperature was raised on a hot plate by setting at 50° C. When the temperature reached the set temperature, the sample was collected in a 1 L Tedlar bag at a predetermined time while leaving the lid of the sample open. The collected samples were evaluated for persistence of fragrance by a panel trained in scent.

TABLE 5

| | Persistence of fragrance |
|---|---|
| Grade | |
| 0 | Odorless |
| 1 | Smell that can be felt slightly (minimum cognitive concentration) |
| 2 | Weak smell to know what it is |
| 3 | Easily recognizable smell |
| 4 | Irritating smell |
| 5 | Strong smell |

Evaluation results of the retention of initial scent and persistence of fragrance are shown in Table 6.

TABLE 6

| | Retention of initial scent | | Persistence of fragrance | |
|---|---|---|---|---|
| Ex. | Initial | After 15 days | Initial | After 15 days |
| Comparative Example 1 | 5 | 3 | 3 | 2 |
| Comparative Example 2 | 5 | 5 | 5 | 5 |
| Comparative Example 3 | 5 | 3 | 5 | 3 |
| Comparative Example 4 | 5 | 2 | 5 | 2 |
| Comparative Example 5 | 5 | 4 | 3 | 2 |
| Example 1 | 5 | 5 | 5 | 5 |
| Example 2 | 5 | 5 | 5 | 5 |
| Example 3 | 5 | 5 | 5 | 4 |
| Example 4 | 5 | 4 | 5 | 4 |
| Example 5 | 5 | 4 | 5 | 4 |
| Example 6 | 5 | 4 | 5 | 4 |

As shown in Table 6, it can be seen that all the compositions according to Examples have excellent retention of initial scent, and relatively excellent initial strength of fragrance and persistence of fragrance.

Experimental Example 3: Evaluation of High Temperature Stability

A sample amount of each composition was taken based on 0.5 g of a fragrant material to have same amount of the fragrant material, and then it was placed in a 70 ml vial. Each of the samples was evaluated in a convection oven at temperature of 50, 70 and 90° C. according to the criteria shown in Table 7, and the results are shown in Table 8.

TABLE 7

| | Criteria of high temperature stability |
|---|---|
| ◎ | Not melt and flow when stored at 90° C. |
| ○ | Not melt and flow when stored at 70° C. |
| Δ | Not melt and flow when stored at 50° C. |
| NG | Melt and flow to be deformed when stored at 50° C. |

TABLE 8

| Ex. | High temperature stability |
|---|---|
| Comparative Example 1 | ◎ |
| Comparative Example 2 | ◎ |
| Comparative Example 3 | ◎ |
| Comparative Example 4 | — |

TABLE 8-continued

| Ex. | High temperature stability |
|---|---|
| Comparative Example 5 | ◉ |
| Example 1 | ◉ |
| Example 2 | ◉ |
| Example 3 | ◉ |
| Example 4 | ○ |
| Example 5 | ◉ |
| Example 6 | ◉ |

Experimental Example 4: Evaluation of Shape Control and Retention

In order to evaluate shape stability of each composition, it was evaluated for powder flying and moldability. A sample amount of each composition was taken based on 0.5 g of a fragrant material to have same amount of the fragrant material, and then it was placed in a 70 ml vial. The sample was placed in a convection oven at 90° C. for 7 days until the fragrant material was sufficiently removed. However, Comparative Examples 4 and 5 and Examples 2, 4 and 5 were placed at 90° C. for 1 day. For each sample from which the fragrant material was removed, powder flying was evaluated according to criteria shown in Table 9, and the results are shown in Table 10.

TABLE 9

| | Criteria of powder flying |
|---|---|
| ◉ | Neither sticking on the surface nor powder flying after removal of fragrant material |
| ○ | Slightly sticking on the surface but no powder flying after removal of fragrant material |
| Δ | Sticking on the surface but no powder flying after removal of fragrant material |
| NG | Powder flying after removal of fragrant material |

TABLE 10

| Ex. | Powder flying | Shape control and retention |
|---|---|---|
| Comparative Example 1 | NG | Impossible to mold |
| Comparative Example 2 | NG | Impossible to mold |
| Comparative Example 3 | ◉ | Limited (Highly shrunk after drying) |
| Comparative Example 4 | — | — |
| Comparative Example 5 | ◉ | Moldable |
| Example 1 | ◉ | Moldable |
| Example 2 | ◉ | Moldable |
| Example 3 | ◉ | Moldable |
| Example 4 | ○ | Moldable |
| Example 5 | ◉ | Moldable |
| Example 6 | ○ | Moldable |

As shown in Table 10, it can be seen that all the compositions according to Examples are moldable. Comprehensively, it can be seen that the initial scent is maintained and persistence of fragrance is improved while having excellent high temperature stability and remarkably improving powder flying phenomenon.

On the other hand, it is found that in Comparative Examples 1 and 2, molding is not possible, in Comparative Example 4 the composition is in the liquid phase, and in Comparative Example 5 molding is possible to some extent but retention and persistence of fragrance are lowered due to the low load rate of the fragrant material as shown in Tables 3 and 6.

Examples 7 to 9 and Comparative Example 6

Examples 7 to 9

A solid fragrance composition was prepared in the same manner as in Example 1, except for using a fragrant material with a weight ratio of lavender oil:vanilla oil:cedarwood oil of 80:15:5 as shown in Table 11.

Comparative Example 6

An oil obtained by mixing Lavender oil, vanilla oil and cedarwood oil in a weight ratio of 80:15:5 was used.

In addition, for each composition according to Examples and Comparative Examples, the load rate was evaluated in the same manner as in Experimental Example 1, and the results are shown in Table 11.

TABLE 11

| Ex. | Fragrant material | Porous Particle | Gel matrix | Gel matrix:Porous particle weight ratio | Load rate of fragrant material |
|---|---|---|---|---|---|
| Example 7 | Lavender essential oil/ Vanilla oil/ Cedarwood oil | Silica 9 g (Average pore diameter 30~40 nm) | Agar 1 g | 1:9 | 250 |
| Example 8 | Lavender essential oil/ Vanilla oil/ Cedarwood oil | Silica 9 g (Average pore diameter 30~40 nm) | Agar 1 g | 1:9 | 250 |
| Example 9 | Lavender essential oil/ Vanilla oil/ Cedarwood oil | Silica 9 g (Average pore diameter 30~40 nm) | Agar 1 g | 1:9 | 250 |
| Comparative Example 6 | Lavender essential oil/ Vanilla oil/ Cedarwood oil | — | — | — | — |

Experimental Example 5: Evaluation of Retention of Fragrance During Aging and Loading of Mixed Fragrance In order to evaluate the degree of deterioration of the initial scent, and the degree of loading of fragrance and retention of fragrance during the aging process, the evaluation was conducted on the mixed fragrance using the same methods as in Experimental Example 2 and the criteria in Table 4. However, the loading time and evaluation time were as shown in Table 11.

For each composition according to Comparative Example 6 and Examples 7 to 9, the change relative to the initial scent was evaluated according to storage period. After combining fragrant materials, aging proceeds over time. In order to obtain the scent emitted during aging, the degree of scent deterioration was evaluated by loading the fragrant material after a certain period of time after mixing fragrant materials. Based on the evaluation score immediately after mixing and loading the fragrant material of 5, the retention of initial scent over time was evaluated and compared.

TABLE 12

| Ex. | Loading time/Evaluation time of fragrance |
|---|---|
| Comparative Example 6 | No loading/Evaluation immediately after mixing, on Day 5, on Day 10, and on Day 15 |
| Comparative Example 7 | Loading immediately after mixing/Evaluation immediately after loading and on Day 15 |
| Comparative Example 8 | Loading on Day 5 of aging/Evaluation immediately after loading and on day 15 |
| Comparative Example 9 | Loading on Day 10 of aging/Evaluation immediately after loading and on Day 15 |

The evaluation results are shown in Tables 13 and 14.

TABLE 13

| | Retention of initial scent | | | |
|---|---|---|---|---|
| Ex. | Immediately after loading | Day 5 | Day 10 | Day 15 |
| Example 7 | 5 | — | — | 5 |
| Example 8 | 5 | — | — | 5 |
| Example 9 | 5 | — | — | 5 |

TABLE 14

| | Retention of initial scent | | | |
|---|---|---|---|---|
| Ex. | Immediately after loading | Day 5 | Day 10 | Day 15 |
| Comparative Example 6 | 5 | 4 | 3 | 3 |

As shown in Table 12, in the case of Comparative Example 6, which is in the form of liquid fragrant material, a change in fragrance was observed as the storage time elapsed after mixing fragrant materials. On the other hand, in Examples 7 to 9, irrespective of the case of loading immediately or at a certain time elapsed after mixing fragrant materials, it is found that there is no change in fragrance over time because the fragrance at the beginning of loading and on Day 15 of loading show the same score. That is, in the case of the mixed liquid fragrant material, the fragrance is continuously deteriorated over time, whereas in the case of the fragrant material loaded by the composition according to the present invention at a specific stage during aging, the fragrance at the time of loading remains unchanged even after 15 days of loading.

As can be seen from the above results, the present invention can improve the load rate, retention of initial scent and persistence of fragrance, especially it can delay or stop aging in order to achieve a desired scent at a specific stage during combining fragrant materials. In addition, by improving both high-temperature stability and shape retention characteristics, various types of products can be provided that can satisfy the needs of consumers while maximizing the purpose of the product.

Therefore, a solid fragrance with improved utility and stability can be freely processed into a required shape and easily applied to various fields.

The above description is merely illustrative of the technical idea of the present invention, and those of ordinary skill in the art to which the present invention pertains can make various modifications and variations without departing from the essential characteristics of the present invention. In addition, the embodiments disclosed in the present invention are not intended to limit the technical idea of the present invention, but to explain the technical idea, and the scope of the technical idea of the present invention is not limited by these embodiments. The scope of protection of the present invention should be interpreted by the following claims, and all technical ideas within the scope equivalent thereto should be construed as being included in the scope of the present invention.

What is claimed is:

1. A solid fragrance composition, comprising:
   porous particles having a plurality of pores,
   a gel matrix for binding the porous particles to each other, wherein the gel matrix has voids, and
   a fragrant material contained in the pores of the porous particles and in the voids of the gel matrix,
   wherein a weight ratio of the gel matrix and the porous particles is 1:3 to 30, wherein an average particle size of the porous particles is 1 to 100 μm, and wherein the voids of the gel matrix have an average void diameter of 0.1 to 100 μm.

2. The solid fragrance composition according to claim 1, wherein the porous particles are at least one selected from the group consisting of silica, zeolite, activated carbon and acrylic resin particles.

3. The solid fragrance composition according to claim 1, wherein the gel matrix is at least one selected from the group consisting of agar, carrageenan, gellan gum and gelatin.

4. The solid fragrance composition according to claim 1, wherein an average pore diameter of the porous particles is 1 to 100 nm.

5. The solid fragrance composition according to claim 1, wherein a load rate of the fragrant material according to Equation 1 is 100 to 500%:

$$\text{Load rate (\%)} = (\text{maximum weight of loaded fragrant material (g)/total weight of the porous particles and the gel matrix (g)}) \times 100 \quad \text{[Equation 1]}.$$

6. A method for manufacturing a solid fragrance composition, comprising:
   1) Dispersing porous particles in water;
   2) Adding a gel matrix to the dispersion of 1) and homogeneously mixing at high temperature to bind the porous particles to each other while forming voids;
   3) Injecting the mixture of 2) into a mold and cooling it to prepare a molded product; and 4) loading a fragrant material into the molded product of 3), wherein a weight ratio of the gel matrix and the porous particle is 1:3 to 30, wherein an average particle size of the porous particles is 1 to 100 μm, and wherein the voids formed in the gel matrix have an average void diameter of 0.1 to 100 μm.

* * * * *